United States Patent
Vijfvinkel et al.

[11] Patent Number: 6,120,147
[45] Date of Patent: Sep. 19, 2000

[54] VITRECTOMY LENS

[75] Inventors: Gerrit Jan Vijfvinkel, Geervliet, Netherlands; Mark W. Furlong, Kingston, N.H.

[73] Assignee: Dutch Ophthalmic Research Center International bv, Netherlands

[21] Appl. No.: 09/271,421

[22] Filed: Mar. 17, 1999

[51] Int. Cl.[7] .............................. G02C 7/04; A61B 3/00
[52] U.S. Cl. .................... 351/160 R; 351/219; 351/177
[58] Field of Search ................................. 351/219, 247, 351/160 R, 160 H, 161, 162, 177

[56] References Cited

U.S. PATENT DOCUMENTS

| | | | |
|---|---|---|---|
| 3,001,441 | 9/1961 | Herbert | 88/20 |
| 3,409,349 | 11/1968 | Boyle et al. | 351/6 |
| 3,820,879 | 6/1974 | Frisen | 351/1 |
| 4,007,980 | 2/1977 | Bracher et al. | 351/6 |
| 4,065,208 | 12/1977 | Currey | 351/6 |
| 4,568,157 | 2/1986 | Kurwa | 351/160 R |
| 4,575,205 | 3/1986 | Rappazzo | 351/219 |
| 4,598,984 | 7/1986 | Rol | 351/219 |
| 4,750,829 | 6/1988 | Wise | 351/160 R |
| 4,966,452 | 10/1990 | Shields et al. | 351/219 |
| 5,022,749 | 6/1991 | Ogura | 351/219 |
| 5,347,326 | 9/1994 | Volk | 351/160 R |
| 5,479,222 | 12/1995 | Volk | 351/219 |
| 5,548,352 | 8/1996 | Dewey | 351/160 H |
| 5,623,323 | 4/1997 | Johnson et al. | 351/219 |
| 5,903,333 | 5/1999 | Siminou et al. | 351/160 R |
| 5,963,301 | 10/1999 | Volk | 351/219 |

OTHER PUBLICATIONS

"Vitrectomy Lens System," Dutch Ophthalmic, USA brochure, one page, at least by Jul. 1998.

"Landers Vitrectomy Lens Ring System," Ocular Instruments, Inc., one page, at least by Jul., 1998.

Abstract, "A Novel In–Sitou–Molded Hydrogel Contact Lens For Vitrectomy," *Investigate Ophthalmology & Visual Science*, vol. 37, No. 3, p. S406, (Feb. 15, 1996).

Peyman, K. J., "A New Contact Lens to Aid Pars Plana Vitrectomy with a Temporary Keratoprosthesis," *Retina*, pp. 355, (1993).

*Primary Examiner*—Georgia Epps
*Assistant Examiner*—Jordan M. Schwartz
*Attorney, Agent, or Firm*—Hamilton, Brook, Smith & Reynolds, PC

[57] ABSTRACT

A self-adhering contact lens made of flexible material for adhering to cornea and scleral regions of the eye includes a central lens portion optically shaped for viewing interior regions of the eye. The central lens portion has an interior concave surface with a radius of curvature $R_1$ for contacting the cornea. An outer flange formed integrally with the central lens portion extends radially outwardly from the central lens portion. The outer flange has an interior concave surface extending from the interior concave surface of the central lens portion. The interior concave surface of the outer flange is designed to contact the sclera and has a radius of curvature $R_2$ that is greater than the radius $R_1$ of. The outer flange is shaped for deflecting relative to the central lens portion for conforming the interior concave surface of the outer flange to the sclera.

31 Claims, 4 Drawing Sheets

VITRECTOMY LENS

BACKGROUND

When performing surgery of the posterior segment of the eye (for example, vitreoretinal surgery), it is typically necessary to view the anatomy of the eye with an operating microscope. Generally, a standard operating microscope is able to view the structures of the anterior segment of the eye and the anterior portion of the posterior segment of the eye, but cannot provide viewing of the entire posterior segment. The reason for this is that the natural optics of the eye (normally consisting of the cornea and the crystalline lens) prevent the operating microscope from focusing on some structures in the posterior segment of the eye such as the retina.

Therefore, in order to focus the operating microscope on structures such as the retina, a vitrectomy lens with the appropriate optical properties is positioned between the eye and the microscope to compensate for the natural optics of the eye. Current vitrectomy lenses are reusable lenses made from optical glass, and in use, are usually held against the eye either with sutures, by hand, or with a silicone ring.

SUMMARY OF THE INVENTION

A drawback with glass vitrectomy lenses is that the lenses can be damaged during cleaning. A scratched or cloudy lens surface will reduce the optical quality of the lens. In addition, the methods of securing such lenses to the eye as described above can be unwieldy.

The present invention is directed to a self-adhering contact lens made of flexible material for adhering to cornea and scleral regions of the eye solely by capillary traction. As a result, separate means for holding the lens against the eye are not required. The lens is inexpensive enough to be disposable so that a new lens is used for each patient, thereby ensuring optimum optics. The lens includes a central lens portion optically shaped for viewing interior regions of the eye. The central lens portion has an interior concave surface with a radius of curvature $R_1$ for contacting the cornea. An outer flange formed integrally with the central lens portion extends radially outwardly from the central lens portion. The outer flange has an interior concave surface extending from the interior concave surface of the central lens portion. The interior concave surface of the outer flange is designed to contact the sclera and has a radius of curvature $R_2$ that is greater than the radius $R_1$. The outer flange is shaped for deflecting relative to the central lens portion for conforming the interior concave surface of the outer flange to the sclera.

In preferred embodiments, the radius of curvature of the sclera is greater than the radius of curvature of the cornea. The radius of curvature $R_1$ of the interior concave surface of the central lens portion approximates the radius of curvature of the cornea, and the radius of curvature $R_2$ of the interior concave surface of the outer flange is less than the radius of curvature of the sclera. The outer flange has a thickness that is sufficiently less than the height of the central lens portion for enabling the outer flange to deflect relative to the central lens portion without substantially deforming the central lens portion.

The ratio of the height of the central lens portion to the thickness of the outer flange is preferably greater than about 7. The height of the central lens portion is preferably about 3.5 mm or greater and the thickness of the outer flange is in the range of 0.4 mm to 0.5 mm. In addition, the ratio of the outer diameter of the central lens portion to the outer diameter of the outer flange is preferably in the range of 0.83 to 0.88. The outer diameter of the central lens portion is preferably about 12 mm and the outer diameter of the outer flange is about 14 mm. Finally, the radii $R_2$ and $R_1$ preferably have a ratio $R_2/R_1$ of about 1.3.

In one preferred embodiment, the central lens portion has a flat exterior surface. In another preferred embodiment, the central lens portion has a concave exterior surface. Finally, in yet another preferred embodiment, the central lens portion has an angled exterior surface.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
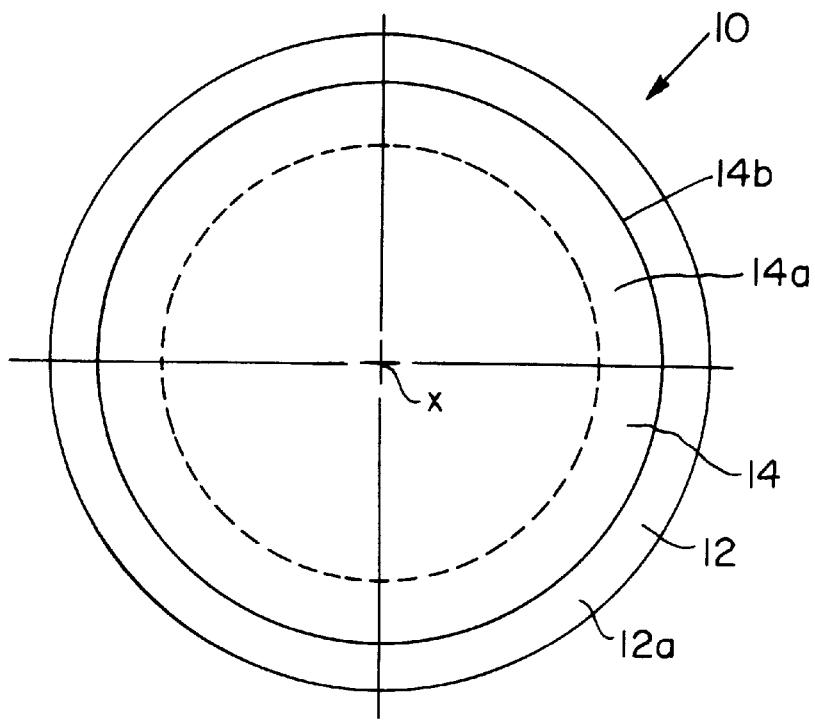
FIG. 1 is a top view of the present invention vitrectomy lens.
Figure 2:
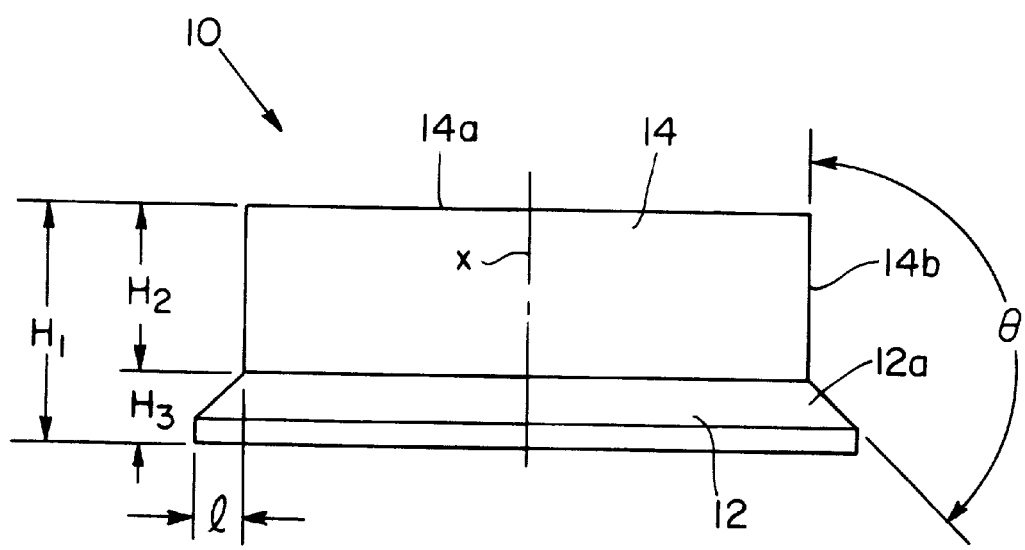
FIG. 2 is a side view of the vitrectomy lens of FIG. 1

Referring to FIGS. 1–4, vitrectomy lens 10 is a generally round one-piece disposable plano lens formed from soft flexible optically clear material. Lens 10 is self-adhering to eye 20 (FIG. 4) through capillary traction and does not require additional means of holding the lens to the eye 20. Lens 10 includes a relatively thick disc-shaped central lens portion 14 and a thin annular outer flange 12 extending outwardly and downwardly from central lens portion 14 at an angle θ. Central lens portion 14 has a circular outer perimeter with a vertical side wall 14b. Central lens portion 14 also has an interior concave surface 18 (FIG. 3) with a radius of a curvature $R_1$ approximating the curvature of the cornea 20a of eye 20 (FIG. 4) for contacting cornea 20a. The exterior surface 14a of central lens portion 14 is flat or planar and is parallel to the bottom of outer flange 12. The design of central lens portion 14 provides optics which allow viewing of the central vitreous and fundus of eye 20.

Figure 3:
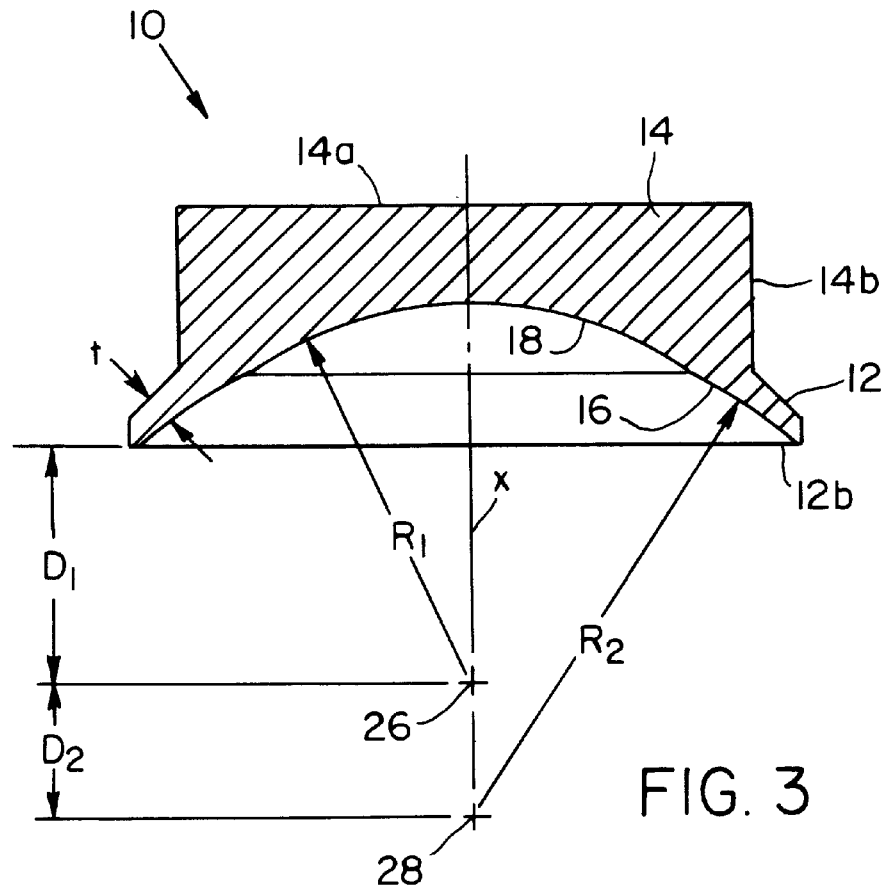
FIG. 3 is a side sectional view of the vitrectomy lens of FIG. 1.

Outer flange 12 includes an annular interior concave surface 16 which is joined to the interior concave surface 18 of central lens portion 14 (FIG. 3). Interior concave surface 16 has a radius of curvature $R_2$ that is larger than the radius of curvature of the cornea 20a and radius $R_1$, but smaller than the radius of curvature of the average sclera 20b. Outer flange 12 has a thickness "t" which is substantially less than the height $H_2$ of central lens portion 14. The large height $H_2$ to thickness "t" difference provides a central lens portion 14 that is relatively stiff in comparison to outer flange 12 so that outer flange 12 can deflect or flex relative to central lens portion 14 without substantially deforming central lens portion 14. By providing the interior concave surface 16 with a radius of curvature $R_2$ that is smaller than the radius of curvature of the average sclera 20b, lens 10 is able to be properly secured to a range of different sized eyes. This is possible because when the interior concave surface 16 engages a sclera having a larger radius of curvature than the interior concave surface 16, the outer flange 12 and interior concave surface 16 are able to deform to match the shape of the sclera 20b.

Figure 4:
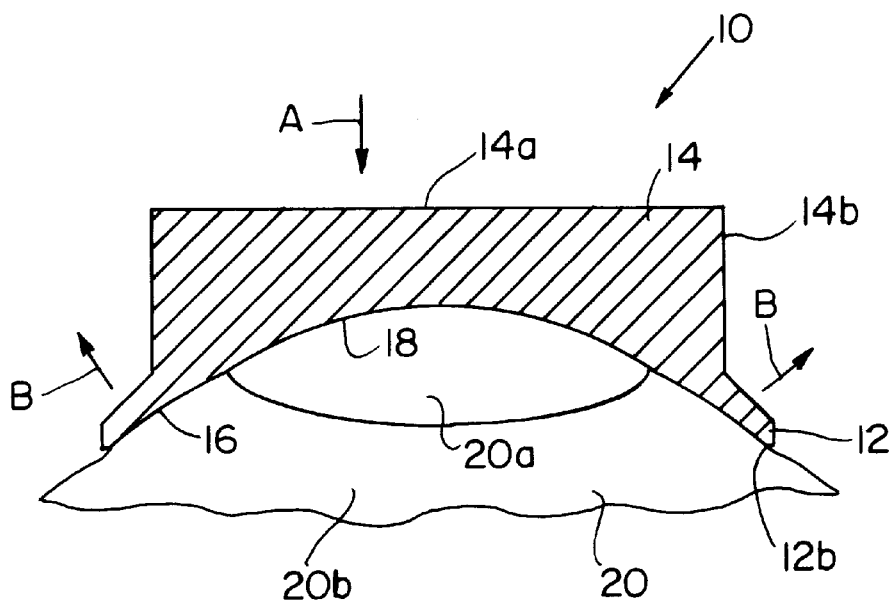
FIG. 4 is a side sectional view of the vitrectomy lens of FIG. 1 adhered to an eye.

In use, referring to FIG. 4, lens 10 is placed upon the eye 20 of the patient. If desired, saline or other more viscous fluids can be first applied to eye 20. Initially, only the bottom of outer flange 12 contacts the eye 20. Since the interior concave surface 16 of outer flange 12 has a radius of curvature $R_2$ that is less than the radius of curvature of the sclera 20b, the bottom interior edge 12b of outer flange 12 contacts the sclera 20b in an annular line of contact. Lens 10 is then pressed in the direction of arrow "A" towards the eye 20 which deflects and deforms outer flange 12 upwardly or outwardly relative to central lens portion 14 (away from eye 20) in the direction of arrows "B". This brings the interior concave surface 18 of central lens portion 14 down into full surface contact against cornea 20a and changes the shape of the interior concave surface 16 of outer flange 12 so that the interior concave surface 16 is in full surface contact against the sclera 20b. Once the interior concave surfaces 16/18 are in contact with the cornea 20a and sclera 20b, interior concave surfaces 16/18 have sufficient surface area to adhere lens 10 to eye 20 solely by capillary traction. The soft flexible material of lens 10 is light weight so that capillary traction can provide a sufficient amount of adhesive force for holding lens 10 in place. A microscope can then be moved into position relative to lens 10 for viewing structures in the interior of eye 20 such as the retina. Lens 10 allows viewing of the central vitreous and fundus of eye 20 in about a 20° field of view.

A more detailed description of lens 10 now follows. In one preferred embodiment, lens 10 is molded from optically clear silicone such as NuSil Med 6033 silicone. The central lens portion 14 is sized to cover the entire cornea 20a of the eye 20 with the outer flange 12 providing the extra surface area required to firmly secure lens 10 to eye 20 by capillary traction. The outer diameter of central lens portion 14 is 12 mm +/−0.2 mm and the outer diameter of outer flange 12 is 14 mm +/−0.2 mm. As a result, outer flange 12 extends outwardly from central lens portion 14 a distance "1" of about 1 mm. The height $H_2$ of central lens portion 14 is about 3.5 mm and the height $H_3$ of outer flange 12 is about 1.5 mm. The overall height $H_1$ of lens 10 is 5 mm +/−0.1 mm. The exterior surface 12a of outer flange 12 extends outwardly and downwardly from central lens portion 14 relative to side wall 14b at an angle $\theta$ that is about 135°. The thickness "t" of outer flange 12 is between about 0.4 mm to 0.5 mm thick. The interior concave surface 18 of the central lens portion 14 is spherical in shape with a radius of curvature $R_1$ of about 7.95 mm. The origin 26 of radius $R_1$ is located along the central axis X below outer flange 12 a distance $D_1$ of about 4.95 mm. The interior concave surface 16 of outer flange 12 also has a spherical curvature with the radius of curvature $R_2$ being about 10.3 mm. The origin 28 of radius $R_2$ is located along central axis X below origin 26 a distance $D_2$ of about 2.74 mm.

With such dimensions, the radii $R_2$ and $R_1$ have a ratio $R_2/R_1$ of about 1.3. In addition, the ratio of the outer diameter of the central lens portion 14 to the outer diameter of the outer flange 12 is in the range of 0.83 to 0.88, with 0.86 being preferred. The ratio of the height $H_2$ of central lens portion 14 to the thickness "t" of outer flange 12 is greater than about 7 and preferably ranges between 7 to 8.75.

Figure 5:
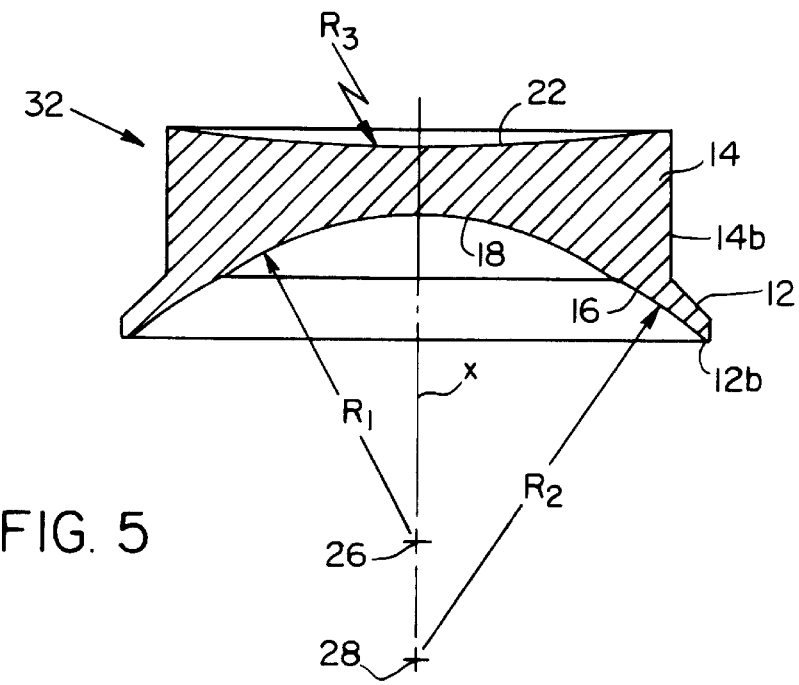
FIG. 5 is a side sectional view of another preferred vitrectomy lens.

Referring to FIG. 5, vitrectomy lens 32 differs from lens 10 in that lens 32 has a shallow exterior concave surface 22 formed on the exterior side of central lens portion 14. Exterior concave surface 22 provides lens 32 with optical properties for viewing a wide field (about a 30° field of view). This makes lens 32 suitable for viewing the posterior fundus and central vitreous of eye 20. In one preferred embodiment, exterior concave surface 22 has a radius of curvature $R_3$ of about 38 mm with the origin of radius $R_3$ located along axis X.

Figure 6:
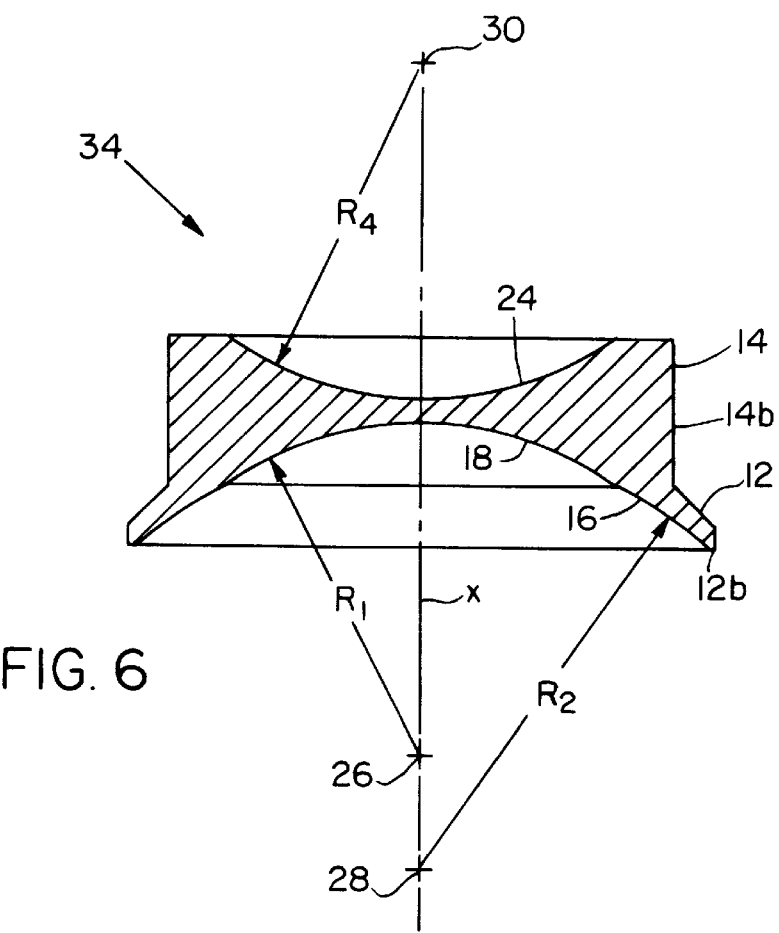
FIG. 6 is a side sectional view of yet another preferred vitrectomy lens.

Referring to FIG. 6, vitrectomy lens 34 differs from lens 32 in that lens 34 has an exterior concave surface 24 that is deeper than the exterior concave surface 22 of lens 32. In addition, exterior concave surface 24 has a radius of curvature $R_4$ that is smaller than radius $R_3$ of exterior concave surface 22. In one preferred embodiment, radius $R_4$ is 7.95 mm and has an origin 30 positioned along axis X about 6.45 mm above central lens portion 14. As a result, exterior concave surface 24 is about 1.5 mm deep. Exterior concave surface 24 provides lens 34 with optical properties for viewing the fundus in an air filled phakic eye.

Although specific dimensions for the radii $R_3/R_4$ of lenses 32/34 have been given, depending upon the application at hand, the dimensions of radii $R_3/R_4$ can vary. For example, the dimensions of $R_3/R_4$ can range between 7.95 mm and 38 mm, and can also be less than 7.95 mm or greater than 38 mm.

Figure 7:
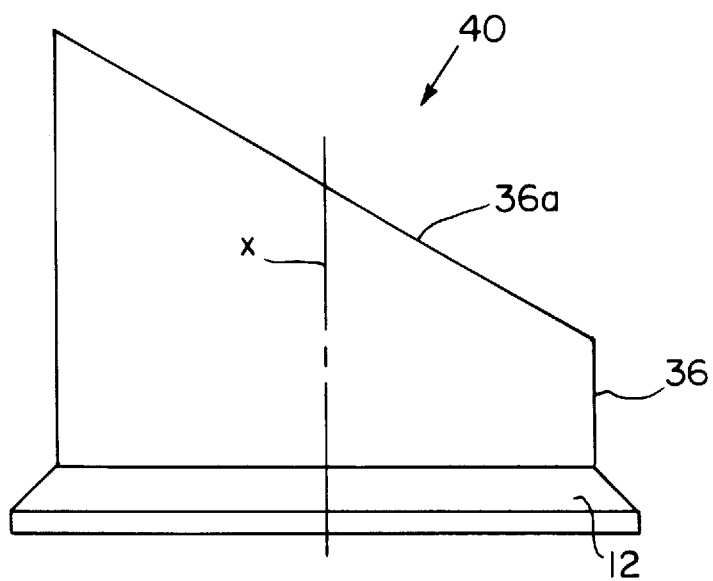
FIG. 7 is a side view of still another preferred vitrectomy lens.
Figure 8:
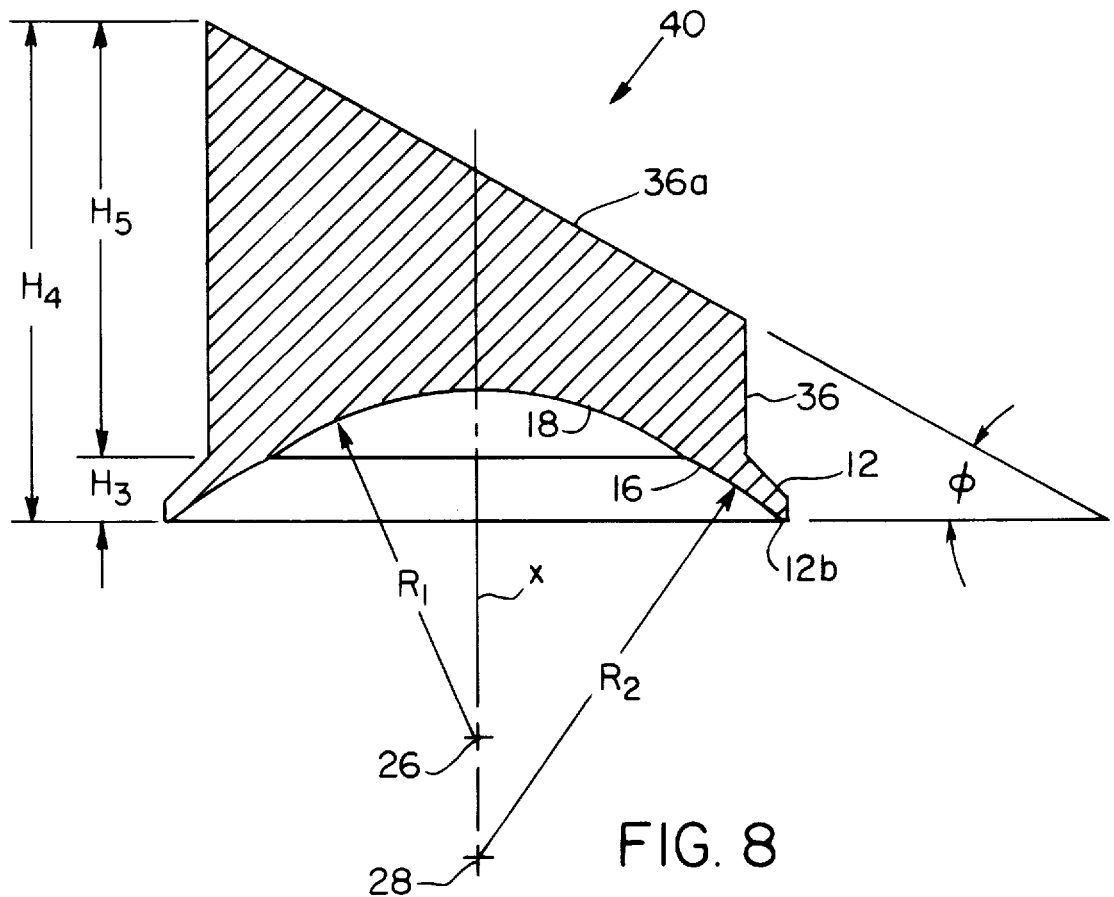
FIG. 8 is a side sectional view of the vitrectomy lens of FIG. 7.

Referring to FIGS. 7 and 8, vitrectomy lens 40 differs from lens 10 in that central lens portion 36 has an angled upper planar surface 36a extending at an angle $\Phi$ relative to the plane of the bottom of outer flange 12. The angled upper planar surface 36a forms a prism-like lens. In one preferred embodiment, upper planar surface 36a is at an angle $\Phi$ of about 30°. This provides peripheral viewing beyond the equator of eye 20. The height $H_5$ of central lens region 36 is about 9.9 mm and the overall height $H_4$ of lens 40 is about 11.4 mm. In other preferred embodiments, upper planar surface 36a can be at an angle $\Phi$ between 15° and 50°, depending upon the application at hand. For example, an angle $\Phi$ of 20° is suitable for viewing the posterior periphery of eye 20.

While this invention has been particularly shown and described with references to preferred embodiments thereof, it will be understood by those skilled in the art that various changes in form and details may be made therein without departing from the spirit and scope of the invention as defined by the appended claims.

For example, although specific dimensions and lens shapes have been given for lenses 10, 32, 34 and 40, such dimensions and lens shapes can vary depending upon the application at hand as well as the size of the patient's eye. Additionally, although lenses 10, 32, 34 and 40 are preferably molded from silicone, other suitable soft optically clear materials can be used such as flexible acrylics. Further, other suitable methods of manufacturing other than molding can be employed such as machining. Also, interior concave surfaces 16/18 have been each shown and described to have a constant radius of curvature, but alternatively, each can have a varying radius of curvature to custom fit the interior concave surfaces 16/18 for a particular patient. Finally, in addition to securing lenses 10, 32, 34 and 40 to a patient's eye with capillary traction, the lenses can also be sutured in place.

What is claimed is:

1. A self-adhering contact lens made of flexible material, the lens for adhering to cornea and scleral regions of an eye, the cornea and sclera each having a radius of curvature, the radius of curvature of the sclera being greater than the radius of curvature of the cornea, the lens comprising:

a central lens portion optically shaped for viewing interior regions of the eye, the central lens portion having an interior concave surface with a radius of curvature $R_1$ approximating the radius of curvature of the cornea for contacting the cornea; and an outer flange formed integrally with the central lens portion extending radially outwardly from the central lens portion, the outer flange having an interior concave surface extending from the interior concave surface of the central lens portion, the interior concave surface of the outer flange for contacting the sclera and having a radius of curvature $R_2$ that is greater than the radius $R_1$ but less than the radius of curvature of the sclera, the outer flange being shaped for deflecting relative to the central lens portion for conforming the interior concave surface of the outer flange to the sclera.

2. The lens of claim 1 in which the central lens portion has a height and the outer flange has a thickness, the thickness of the outer flange being sufficiently less than the height of the central lens portion for enabling the outer flange to deflect relative to the central lens portion without substantially deforming the central lens portion.

3. The lens of claim 2 in which the lens has a ratio of the height of the central lens portion to the thickness of the outer flange of greater than about 7.

4. The lens of claim 3 in which the height of the central lens portion is 3.5 mm or greater and the thickness of the outer flange is in the range of 0.4 mm to 0.5 mm.

5. The lens of claim 1 in which central lens portion and the outer flange each have an outer diameter, the lens having a ratio of the outer diameter outer of the central lens portion to the outer diameter outer or the outer flange in the range of 0.83 to 0.88.

6. The lens of claim 5 in which the outer diameter of the central lens portion is about 12 mm and the outer diameter of the outer flange is about 14 mm.

7. The lens of claim 1 in which the radii $R_2$ and $R_1$ have a ratio $R_2/R_1$ of about 1.3.

8. The lens of claim 1 in which the central lens portion has a flat exterior surface.

9. The lens of claim 1 in which the central lens portion has a concave exterior surface.

10. The lens of claim 9 in which the concave exterior surface has a radius of curvature in the range of 7.95 mm to 38 mm.

11. The lens of claim 1 in which the central lens portion has an angled exterior surface.

12. The lens of claim 11 in which the angled exterior surface is in the range of 15° to 50°.

13. A self-adhering contact lens made of flexible material, the lens for adhering to cornea and scleral regions of an eye, the cornea and sclera each having a radius of curvature, the radius of curvature of the sclera being greater than the radius of curvature of the cornea, the lens comprising:

a central lens portion optically shaped for viewing interior regions of the eye, the central lens portion having an interior concave surface with a radius of curvature $R_1$ approximating the radius of curvature of the cornea for contacting the cornea, the central lens portion having a height; and an outer flange formed integrally with the central lens portion extending radially outwardly and downwardly from the central lens portion, the outer flange having an interior concave surface extending from the interior concave surface of the central lens portion, the interior concave surface of the outer flange for contacting the sclera and having a radius of curvature $R_2$ that is greater than the radius $R_1$ but less than the radius of curvature of the sclera, the outer flange having a thickness that is sufficiently less than the height of the central lens portion for enabling the outer flange to deflect relative to the central lens portion for conforming the interior concave surface of the outer flange to the sclera without substantially deforming the central lens portion.

14. The lens of claim 13 in which the lens has a ratio of the height of the central lens portion to the thickness of the outer flange of greater than about 7.

15. The lens of claim 14 in which the height of the central lens portion is 3.5 mm or greater and the thickness of the outer flange is in the range of 0.4 mm to 0.5 mm.

16. The lens of claim 13 in which central lens portion and the outer flange each have an outer diameter, the lens having a ratio of the outer diameter of the central lens portion to the outer diameter of the outer flange in the range of 0.83 to 0.88.

17. The lens of claim 16 in which the outer diameter of the central lens portion is about 12 mm and the outer diameter of the outer flange is about 14 mm.

18. The lens of claim 13 in which the central lens portion has a flat exterior surface.

19. The lens of claim 13 in which the central lens portion has a concave exterior surface with a radius of curvature in the range of 7.95 mm to 38 mm.

20. The lens of claim 13 in which the central lens portion has an exterior surface angled in the range of 15° to 50°.

21. The lens of claim 13 in which the radii $R_2$ and $R_1$ have a ratio $R_2/R_1$ of about 1.3.

22. A self-adhering contact lens made of flexible material for adhering to first and second regions of an eye, the first and second regions each having a radius of curvature, the radius of curvature of the second region being greater than the radius of curvature of the first region, the lens comprising:

a central lens portion optically shaped for viewing interior regions of the eye, the central lens portion having an interior concave surface with a radius of curvature $R_1$ approximating the radius of curvature of the first region of the eye for contacting the first region of the eye; and an outer flange formed integrally with the central lens portion extending radially outwardly from the central lens portion, the outer flange having an interior concave surface extending from the interior concave surface of the central lens portion, the interior concave surface of the outer flange for contacting the second region of the eye and having a radius of curvature $R_2$ that is greater than the radius $R_1$ but less than the radius of curvature of the second region of the eye, the outer flange being shaped for deflecting relative to the central lens portion for conforming the interior concave surface of the outer flange to the second region of the eye.

23. A method of forming a self-adhering contact lens made of flexible material, the lens for adhering to cornea and scleral regions of an eye, the cornea and sclera each having a radius of curvature, the radius of curvature of the sclera being greater than the radius of curvature of the cornea, the method comprising:

providing a central lens portion optically shaped for viewing interior regions of the eye, the central lens portion having an interior concave surface with a radius of curvature $R_1$ approximating the radius of curvature of the cornea for contacting the cornea;

forming an outer flange integrally with the central lens portion, the outer flange extending radially outwardly from the central lens portion, the outer flange having an interior concave surface extending from the interior concave surface of the central lens portion, the interior concave surface of the outer flange for contacting the sclera and having a radius of curvature $R_2$ that is greater than the radius $R_1$ but less than the radius of curvature of the sclera; and shaping the outer flange to enable deflection relative to the central lens portion for conforming the interior concave surface of the outer flange to the sclera.

24. The method of claim 23 in which the central lens portion has a height, the method further comprising the step of forming the outer flange with a thickness sufficiently less than the height of the central lens portion for enabling the outer flange to deflect relative to the central lens portion without substantially deforming the central lens portion.

25. The method of claim 24 further comprising the step of forming the central lens portion and the outer flange to have a height to thickness ratio of greater than 7.

26. The method of claim 23 in which the central lens portion and the outer flange each have an outer diameter, the method further comprising the step of forming the central lens portion and the outer flange to have an outer diameter ratio in the range of 0.83 to 0.88.

27. The method of claim 23 further comprising the step of providing the central lens portion with a flat exterior surface.

28. The method of claim 23 further comprising the step of providing the central lens portion with a concave exterior surface.

29. The method of claim 23 further comprising the step of providing the central lens portion with an angled exterior surface.

30. The method of claim 23 further comprising the step of forming the radii $R_2$ and $R_1$ to have a ratio $R_2/R_1$ of about 1.3.

31. A method of securing a self-adhering contact lens made of flexible material to cornea and scleral regions of an eye, the cornea and sclera each having a radius of curvature, the radius of curvature of the sclera being greater than the radius of curvature of the cornea, the method comprising the steps of:

providing a contact lens comprising a central lens portion optically shaped for viewing interior regions of the eye, the central lens portion having an interior concave surface with a radius of curvature $R_1$ approximating the radius of curvature of the cornea, and an outer flange formed integrally with the central lens portion extending radially outwardly from the central lens portion, the outer flange having an interior concave surface extending from the interior concave surface of the central lens portion, the interior concave surface of the outer flange having a radius of curvature $R_2$ that is greater than the radius $R_1$ but less than the radius of curvature of the sclera, the outer flange being shaped for deflecting relative to the central lens portion;

positioning the lens on the eye with a perimeter portion of the outer flange contacting the sclera along a line of contact and the interior concave surface of the central lens portion being above the cornea; and pressing the lens against the eye for deflecting the outer flange relative to the central lens portion to bring the interior concave surface of the central lens portion into contact with the cornea and to conform the interior concave surface of the outer flange into full contact with the sclera, the interior concave surfaces of the central lens portion and the outer flange providing sufficient surface area to secure the lens to the eye by capillary traction.

* * * * *

UNITED STATES PATENT AND TRADEMARK OFFICE
CERTIFICATE OF CORRECTION

PATENT NO. : 6,120,147
DATED : September 19, 2000
INVENTOR(S) : Gerrit Jan Vijfvinkel and Mark W. Furlong It is certified that error appears in the above-identified patent and that said Letters Patent is hereby corrected as shown below:

Claim 5, column 5, line 36, after "outer diameter" delete "outer".

Claim 5, column 5, line 37, after "outer diameter" delete "outer or" and insert ---of---.

Signed and Sealed this

Twenty-fourth Day of April, 2001

Attest:

NICHOLAS P. GODICI

*Attesting Officer*     *Acting Director of the United States Patent and Trademark Office*